(12) United States Patent
Aygen

(10) Patent No.: US 7,033,838 B2
(45) Date of Patent: Apr. 25, 2006

(54) **METHOD FOR THE DIAGNOSIS OF *HELICOBACTER PYLORI* INFECTION, AND A DIAGNOSTIC KIT FOR PERFORMING THE METHOD**

(76) Inventor: Sitke Aygen, Gottfried-Hagen-Str. 60-62, Cologne (DE) D-51105

( * ) Notice: Subject to any disclaimer, the term of this patent is extended or adjusted under 35 U.S.C. 154(b) by 190 days.

(21) Appl. No.: 10/214,323

(22) Filed: Aug. 8, 2002

(65) Prior Publication Data

US 2003/0032081 A1 Feb. 13, 2003

Related U.S. Application Data

(60) Provisional application No. 60/312,541, filed on Aug. 16, 2001.

(30) Foreign Application Priority Data

Aug. 9, 2001 (DE) ................. 101 39 299

(51) Int. Cl.
*G01N 31/10* (2006.01)
*G01N 33/537* (2006.01)
*A01N 47/28* (2006.01)

(52) U.S. Cl. .............. 436/37; 435/7.92; 514/588
(58) Field of Classification Search ............... 436/37; 424/184.1, 190.1, 93.4, 236.1; 530/388.4; 435/69.1, 6, 7.92; 514/588; 536/22.1
See application file for complete search history.

(56) References Cited

U.S. PATENT DOCUMENTS

| | | | |
|---|---|---|---|
| 5,542,419 A * | 8/1996 | Moulton-Barrett et al. | 600/366 |
| 5,928,167 A | 7/1999 | Wagner et al. | |
| 6,113,875 A | 9/2000 | Nyström et al. | |
| 6,171,811 B1 * | 1/2001 | Becerro De Bengoa Vallejo | 435/34 |

FOREIGN PATENT DOCUMENTS

| | | |
|---|---|---|
| DE | 296 13 373 U1 | 11/1996 |
| EP | 0 881 491 A1 | 12/1998 |

OTHER PUBLICATIONS

Chey et al. "The $^{13}$C-Urea Blood Test Accurately Detects Active Helicobacter pylori Infection: A United States, Multicenter Trial", American Journal of Gastroenterology, 94, No. 6 (1999), 1522-1524.
BIOSIS Abstract 2000: 5261.80; *Alimentary Pharmacology & Therapeutics, 14,* Supp. 3, 12-22 (2000) (Vaira et al.).
Cutler, A.F. and Toskes, P., MD, "Comparison of [$^{13}$C] Urea Blood Test to [$^{13}$C] Urea Breath Test for the Diagnosis of Heliobacter pylori", American Journal of Gasterology, 94, No. 4 (1999), 959-61.
EMBASE Abstract 1999197569, *American Journal of Gastroenterology, 94, 1522-1524 (1999)* (Chey et al.).

\* cited by examiner

*Primary Examiner*—Lynette R. F. Smith
*Assistant Examiner*—Lakia J. Tongue
(74) *Attorney, Agent, or Firm*—Jacobson Holman PLLC

(57) ABSTRACT

The method for the diagnosis of *Helicobacter pylori* infection by the oral administration of defined amounts of $^{13}$C-labeled urea and examination for $^{13}$C content of blood samples removed at a defined time is effected by
a) removing from 0.1 to 0.6 ml of capillary blood from the finger or ear lob of a patient or venous blood of a patient, in both cases with an empty stomach before the beginning of the test;
b) administering an exact amount of from 10 to 50 mg of $^{13}$C-urea in aqueous solution with a pH value of 2 to 4 to the patient;
c) again removing capillary or venous blood exactly after 10 to 15 min from the administration; and
d) determining the $^{13}$C content of the blood samples by isotope ratio mass spectrometry (IRMS), and deducing the presence of *Helicobacter pylori* from the increase of the $^{13}$C values.

3 Claims, No Drawings

METHOD FOR THE DIAGNOSIS OF *HELICOBACTER PYLORI* INFECTION, AND A DIAGNOSTIC KIT FOR PERFORMING THE METHOD

This application claims the benefit of Provisional Application No. 60/312,514, filed Aug. 16, 2001.

The present invention relates to a method for the diagnosis of *Helicobacter pylori* infection by the oral administration of defined amounts of $^{13}$C-labeled urea and examination for $^{13}$C content of blood samples removed at a defined time.

The previously usual and mostly performed method for the diagnosis of *Helicobacter pylori* infection is the $^{13}$C-urea respiration test. This method has been described in detail in EP-A-0 253 927. This test has the disadvantage, that it cannot be applied for children below 3 years and adults suffering from breathinsufficiency like asthma.

Rex Moulton-Barrett et al., The American Journal of Gastroenterology, Vol. 88, 1993, pages 369 to 374, describe a method in which $^{13}$C-labeled hydrogencarbonate is determined in the serum upon oral administration of $^{13}$C-labeled urea. In this test, 5 mg/kg of $^{13}$C-labeled urea was administered to the patient, and blood samples of 3 ml each were taken and examined after 15, 30, 60, 90, 120 and 180 min. This method has been further examined and described by Mark J. Kim et al. in Gastroenterology 1997, 113: 31–37, W. D. Chey et al. in The American Journal of Gastroenterology, Vol. 94, 1999, pages 1522 to 1524, Alan F. Cuttler et al. in The American Journal of Gastroenterology, Vol. 94, 1999, pages 959 to 961, and has resulted in the introduction of a test by the company Metabolic Solutions Inc., Nashua, N.H. In this test, without determination of the zero value and upon administration of a high-fat test meal "Ensure", 125 mg of $^{13}$C-urea is administered, and the $^{13}$C content of 3 ml of blood is determined after 30 min. However, due to the low accuracy and precision and due to the very high price of the necessary amount of $^{13}$C-urea and the relatively high test quantity of blood, this test was not successful economically, so that the respiration test remained the mostly used test method despite of all its disadvantages.

It has been the object of the invention to provide a method for the diagnosis of *Helicobacter pylori* infection with as low as possible an amount of $^{13}$C-urea and as low as possible a blood quantity for the examination of the $^{13}$C content, which method establishes the diagnosis of *Helicobacter pylori* infection more simply, more inexpensively, more accurately and more quickly.

This object is now achieved by removing from 0.1 to 0.6 ml of capillary blood from the finger or ear lob of a patient or venous blood, in both cases with an empty stomach before the beginning of the test, administering an exact amount of from 10 to 50 mg of $^{13}$C-urea in aqueous solution with a pH value of 2 to 4 to the patient, again removing capillary or venous blood exactly after 10 to 15 min from the administration, and determining the $^{13}$C content of the blood samples by isotope ratio mass spectrometry (IRMS), and deducing the presence of *Helicobacter pylori* from the increase of the $^{13}$C values.

Even when 0.6 ml of capillary blood and 50 mg of $^{13}$C-urea is used, this method is clearly superior to the previous method, all the more so since the accuracy of the method is enormously increased by determining the starting value, and the method is significantly abbreviated for the patient by the removal of a second blood sample already after 10 to 15 min. In elder patients, the recovery of capillary blood sometimes involves difficulties. In such cases, the method can also be performed with the same small amount of venous blood.

Of critical importance in the method according to the invention is the omission of the high-fat test meal. Instead, the labeled urea is administered in an aqueous solution with a pH value of from 2 to 4. This can be done, for example, either by adjusting the aqueous solution of the labeled urea by means of a non-volatile, pharmacologically acceptable organic acid to a pH value of from 2 to 4, or by adding a pack of a solid pharmacologically acceptable organic acid to the freshly prepared solution. Citric acid has been found particularly suitable. However, in principle, other organic acids of that kind, such as ascorbic acid, are also capable of adjusting the desired pH value. It is also possible to achieve this low pH value by the use of orange juice, grapefruit juice or sour apple juice.

The determination of the $^{13}$C content in the blood samples can be effected, for example, by adding a strong non-volatile acid, such as phosphoric acid, which is capable to release the carbon dioxide in a gaseous form from the blood sample, so that it can be measured with an IRMS device.

However, it is also possible to recover serum from the blood samples, to remove high molecular weight components from the serum sample by means of suitable filters, and to determine the $^{13}$C content in the remaining liquid by a preliminary elemental analysis followed by isotope ratio mass spectrometry.

By comparative examinations, it was established that the detection of a *Helicobacter pylori* infection in a respiratory test is positive when the value of $^{13}$C in the respiratory air is about 4% above the starting value. In contrast, the method according to the invention is capable of detecting *Helicobacter* infections when the difference of the $^{13}$C content is as low as 2.0%. It is obvious that the substantially lower amount of the expensive $^{13}$C-urea, on the one hand, and the quickening of the time of the second sampling from 30 min to 10 min are of significant importance to both the patients and the physicians. In addition, the removal of a maximum of 0.6 ml of capillary or venous blood is significantly simpler and more convenient than the removal of 3 ml of venous blood in the test of the Metabolic Solutions Inc. As compared to this test, above all, the significantly higher accuracy and precision is of critical importance since the starting value is determined for each patient rather than using the average values, which are accompanied by considerable variations and influenced by the different foods taken up by the subjects.

The diagnostic kit according to the invention for performing the method preferably consists of an acidic aqueous solution having a pH value of from 2 to 4 and containing exactly from 10 to 50 mg of 13C-urea, a patient instruction sheet, two sample vessels for receiving the blood samples, and optionally a blood-sampling device. It is decisive that the kit contains an exact amount of 13C-urea. A kit for children may contain less than for adults in the over all range of 10 to 50 mg 13C-urea. Also the time difference between the two removals of blood should be exactly measured. Different kits, however, may be run in the over all time range of 10 to 15 min.

Another preferred embodiment comprises instead of the ready acidic solution a container for urea with exactly from 10 to 50 mg of $^{13}$C-urea and a pack of a solid pharmacologically acceptable organic acid, such as citric acid. Normally, 2 g of citric acid in 200 ml of water or 200 ml of orange juice, grapefruit juice or sour apple juice is suitable for dissolving from 30 to 50 mg of $^{13}$C-urea. Especially for children, the amount of $^{13}$C-urea can be further decreased down to 10 mg.

The blood samples preferably are taken up in commercially available sample vessels for receiving blood samples, for example, Vacutainer®. Preferably, they may already contain the necessary amount of concentrated phosphoric acid, so that the $CO_2$ is immediately released from the blood sample. In principle, however, it is also possible to add a strong non-volatile acid later to the sample vessel for receiving the blood sample.

The determination of the $^{13}$C content is then effected by IRMS directly from the gas phase. An increase of the $^{13}$C content of as low as 2% after 10 min indicates infection with *Helicobacter pylori*.

Alternatively, serum may also be withdrawn from the blood sample after a short settling period. All macromolecules and especially the lipids can be removed from this serum sample by ultrafiltration. The remaining liquid is then first subjected to elemental analysis by combustion, and the $CO_2$ released thereby is again examined by IRMS for the isotope ratio $^{13}C/^{12}C$. In this test method, infection with *Helicobacter pylori* can be detected at an increase of the $^{13}$C content of as low as from 1 to 1.5%.

The higher sensitivities and accuracies of the test method achieved according to the invention can be explained afterwards by the fact that the $^{13}$C content of the labeled urea is to a lesser extent diluted with other carbon sources. This dilution effect is strongest in the respiratory air test and least in the examination of serum samples from which macromolecular molecules are removed by ultrafiltration. Nevertheless, the method in which $CO_2$ is released from the blood sample by a strong non-volatile acid and determined in the gas phase is already excellently suitable for achieving the object of the present invention.

When the method according to the invention is performed in practice, the blood tests are executed by the physician before and from 10 to 15 min after administration of the $^{13}$C-urea. The Vacutainers® can be collected and sent to a central laboratory where the determination of the $^{13}$C contents is effected. From these results fed-back to the physician, he can diagnose whether or not there is an infection with *Helicobacter pylori*.

In principle, all highly sensitive isotope mass spectrometers available on the market can be used for the IRMS determination; however, due to their high price, they can be set up only in central laboratories. Already for clinics, investment in such devices cannot be expected. In contrast, the collecting and analyzing of samples in central laboratories does not involve any problems today in terms of logistics and prices, and the same applies to the back transmission of analytical data to the submitting physician or the submitting clinic.

The same is true of the determination method in the serum from which high molecular weight components have been removed by ultrafiltration. The preliminary elemental analysis by combustion can be performed in central laboratories without problems. The recovery of serum from capillary or venous blood and ultrafiltration can be performed without problems at least in clinics.

For the actual determination of the $^{13}$C content, 20 µl of serum is sufficient and will yield telling results already for an increase of from 1 to 1.5% of $^{13}$C.

The invention claimed is:

1. A method for the diagnosis of *Helicobacter pylori* infection comprising, on a patient with an empty stomach, the sequential steps of:
   a) removing a $1^{st}$ sample of 0.1 to 0.6 ml of capillary or venous blood from the patient;
   b) administering exactly 10 to 50 mg of $^{13}$C-urea in aqueous solution having a pH of 2 to 4 to the patient;
   c) removing a $2^{nd}$ sample of capillary or venous blood from the patient 10 to 15 min after the administering step;
   d) determining the $^{13}$C content of the blood samples in a single measurement of each blood sample by isotope ratio mass spectrometry (IRMS);
   e) diagnosing *Heliobacter pylori* infection when a greater $^{13}$C content is measured in the $2^{nd}$ sample, compared to the $^{13}$C content measured in the $1^{st}$ sample.

2. The method according to claim 1, wherein a strong non-volatile acid which releases $CO_2$ in a gaseous form is added to the samples, and wherein the $^{13}$C content is determined in a gas phase.

3. The method according to claim 1, wherein serum is recovered from the blood samples, high molecular weight components are removed from the serum by filters, and the $^{13}$C content is determined in the filtered serum by a preliminary elemental analysis followed by mass spectrometry.

* * * * *